United States Patent [19]

Gates

[11] Patent Number: 5,408,744

[45] Date of Patent: Apr. 25, 1995

[54] SUBSTRATE FOR A SINTERED ELECTRODE

[75] Inventor: James T. Gates, Maple Grove, Minn.

[73] Assignee: Medtronic, Inc., Minneapolis, Minn.

[21] Appl. No.: 56,448

[22] Filed: Apr. 30, 1993

[51] Int. Cl.$^6$ ............................................. H01R 43/00
[52] U.S. Cl. .......................................... 29/875; 29/885
[58] Field of Search ................................... 29/875, 885

[56] References Cited

U.S. PATENT DOCUMENTS

| | | | |
|---|---|---|---|
| 3,476,116 | 11/1969 | Parsonnet et al. | 128/417 |
| 4,010,758 | 3/1977 | Rockland et al. | 128/418 |
| 4,149,542 | 4/1979 | Thoren | 128/418 |
| 4,440,178 | 4/1984 | Bussard et al. | 128/784 |
| 4,444,206 | 4/1984 | Gold | 128/784 |
| 4,502,492 | 3/1985 | Bornzin | 128/785 |
| 4,506,680 | 3/1985 | Stokes | 128/786 |
| 4,577,642 | 3/1986 | Stokes | 128/784 |
| 4,603,704 | 8/1986 | Mund et al. | 128/784 |
| 4,606,118 | 8/1986 | Cannon et al. | 29/825 |
| 4,677,989 | 7/1987 | Robblee | 128/784 |
| 4,711,251 | 12/1987 | Stokes | 128/784 |
| 4,773,433 | 9/1988 | Richter et al. | 128/784 |
| 4,784,160 | 11/1988 | Szilagyi | 128/784 |
| 4,784,161 | 11/1988 | Skalsky et al. | 128/785 |
| 4,819,661 | 4/1989 | Heil, Jr. et al. | 128/786 |
| 4,819,662 | 4/1989 | Heil, Jr. et al. | 128/786 |
| 4,934,381 | 6/1990 | MacGregor | 128/784 |
| 4,936,317 | 6/1990 | MacGregor | 128/784 |
| 5,097,843 | 3/1992 | Soukup et al. | 128/784 |
| 5,282,844 | 2/1994 | Stokes et al. | 607/120 |

OTHER PUBLICATIONS

Furman, et al., "Decreasing Electrode Size and Increasing Efficiency of Cardiac Stimulation", Journal of Surgical Research, vol. 11, No. 3, Mar. 1971, pp. 105–110.

W. Irnich, "Considerations in Electrode Design for Permanent Pacing", Cardiac Pacing Proceedings of the Fourth International Symposium of Cardiac Pacing, pp. 268–274.

Lindemans, et al., "Acute Voltage, Charge and Energy Thresholds as Functions of Electrode Size for Electrode Stimulation of the Canine Heart", CV Research, vol. XIII, No. 7 pp. 383–391.

Stokes, Kenneth Blaine, "Preliminary Studies on a New Steroid Eluting Epicardial Electrode", Pace, vol. 11, Nov. 1988, Part II, pp. 1797–1803.

*Primary Examiner*—Kenneth J. Ramsey
*Attorney, Agent, or Firm*—Michael J. Jaro; Harold R. Patton

[57] ABSTRACT

A substrate for use in a pacing lead having a sintered porous platinized steroid eluting electrode. The substrate has at least one raised surface which provides an advantageous mounting portion for the sintered electrode. In the preferred embodiment the mounting portion is nailhead-shaped. The present invention provides an electrode produced with increased dimensional consistency, mechanical strength and impedance as compared to electrodes having a straight wire substrate. Also disclosed is a method of manufacturing such an electrode.

14 Claims, 6 Drawing Sheets

SUBSTRATE FOR A SINTERED ELECTRODE

BACKGROUND OF THE INVENTION

1. Field of the Invention

This invention relates generally to chronically implanted medical leads and, in particular, to a substrate which provides increased dimensional consistency and impedance as well as simplifying manufacture of a sintered porous platinized steroid eluting electrode used in a pacing cardiac lead.

2. Description of the Prior Art

The safety, efficacy and longevity of an implanted pacemaker system depends, in part, on the performance of the pacing leads, the electronic circuits and the integrity of the pulse generator, and the capacity and reliability of the pulse generator power source. These interrelated components of the implanted pacemaker system optimally are matched in a fashion that accommodates ever increasing demands on the modes of operation and function of the system in conjunction with an overall reduction in system size, an increase in system longevity and an increased expectation in system reliability. During the past thirty years, the technology of cardiac pacing has significantly advanced. Implantable pacing systems offer ever increasing variety of pacing modalities, thereby substantially broadening the indications for pacemaker use. In conjunction with this advancement, there has been extensive research and development expended to optimize the performance of pacing leads and their reliability while concurrently simplifying their manufacture.

In the past ten years, substantial improvements in reliable stable chronic pacemaker sensing and stimulation thresholds have been achieved which in turn have allowed the development of smaller and longer-lived pacemakers that can be used with leads having excellent safety margins and reliability. As new circuits are developed with lower "overhead" current drains, however, and as the circuits increase in complexity to allow for ever increasing pacemaker capabilities in their programmable functions, modes and memory, pacemaker longevity depends increasingly more on the characteristics of the lead. In addition, many doctors who implant pacemakers prefer that pacing lead bodies be made ever thinner, to occupy less space in the venous system, without diminishing or detracting from the mechanical strength and integrity of the lead body.

In the early days of cardiac pacing, pacing leads having relatively very high geometric surface area electrodes were employed with relatively bulky and short-lived pulse generators. Early investigators, including Dr. Victor Parsonnet, advanced designs of pacing lead electrodes for achievement of low polarization and low thresholds while presenting a relatively small effective surface area for the delivery of a stimulating impulse in designs known as a differential current density (DCD) electrode of the type shown in U.S. Pat. No. 3,476,116. The DCD electrode (like all pacing electrodes of the time) suffered unacceptable chronic tissue inflammation and instability in clinical testing and was not commercialized.

Subsequent researchers, including Dr. Werner Irnich, explored in considerable detail the electrode-tissue interface and sought to arrive at an optimum exposed electrode surface area for both stimulation thresholds and sensing. In his work "Considerations in Electrode Design for Permanent Pacing" published in *Cardiac Pacing; Proceedings of the Fourth International Symposium of Cardiac Pacing* (H. J. Thalen, Ed.) 1973, pp. 268–274, Dr. Irnich argued that the field strength (E) required to stimulate cardiac tissue varies according to the following equation:

$$E = \frac{v}{r} [1/(r + d)]^2$$

where v equals applied voltage (threshold, v), r equals electrode radius and d equals fibrous capsule thickness. Dr. Irnich further argued the mean value for d equals about 0.7 mm, regardless of electrode radius. Therefore, the smaller the electrode radius, the lower the threshold (assuming E is a constant) until r equals d. When $r < d$, thresholds rise again. Dr. Irnich concluded the exposed hemispherical electrode at the tip of the lead should have a radius in the order of 0.7 to 1.0 mm which would result in an exposed surface area of 3–6 $mm^2$. However, Dr. Irnich went on in his article to propose a design employing wire hooks designed to penetrate the myocardium to hold the electrode in position. These active fixation wire hook electrodes never achieved popularity and were supplanted by passive fixation tined and active fixation screw-in endocardial pacing leads.

In a later paper, "Acute Voltage, Charge and Energy Thresholds as Functions of Electrode Size for Electrical Stimulation of the Canine Heart", by F. W. Lindemarts and A. N. E. Zimmerman; *Cardiovascular Research*, Vol. XIII, No. 7, pp. 383–391, July 1979, the authors demonstrated an electrode radius of about 0.5 mm is optimal in the acute situation. However, it was recognized the benefits of a small electrode surface area would be lost when the fibrous capsule gets thicker than about 0.5 mm (as Dr. Irnich also stated.) For that reason electrodes of such small surface area, the authors concluded, could not be used chronically.

Dr. Seymour Furman also studied the relationship of electrode size and efficiency of cardiac stimulation and presented a-ball-tip/exposed spaced coil electrode and a small hemispheric electrode in his article entitled "Decreasing Electrode Size and Increasing Efficiency of Cardiac Stimulation" in *Journal of Surgical Research*, Vol. 11, No. 3, March 1971, pp. 105–110. Dr. Furman concluded the practical lower limit of electrode surface area was in the range of 8 $mm^2$, observing that impedance increased as an inverse function of the surface area.

Electrodes of many shapes including cylindrical, ball-tip, corkscrew, ring tip and open cage or "bird cage" configurations were pursued with exposed electrode surface areas tending toward 8 $mm^2$ in the mid-1970's.

More recently, various investigators have emphasized materials and their relationship to the considerations involved in optimizing electrode design. For example, Bornzin, U.S. Pat. No. 4,502,492 owned by Medtronic, Inc. discloses a low polarization, low threshold electrode design which was commercialized as the TARGET TIP ® lead during the early to mid-1980's. That design featured a generally hemispherical electrode with circular grooves, fabricated from platinum and coated over its external surface with a plating of platinum black. This combination of the relatively low (8 $mm^2$) macroscopic electrode surface area and relatively high microscopic electrode surface area (due to the use of platinum black-) contributed to the achievement of state-of-the-art thresholds for that time period. Other manufacturers marketed electrodes of other materials and configurations including totally porous platinum mesh (Cardiac Pacemakers, Inc.), porous surface sintered (Cordis Corporation), glassy and vitreous carbons (Siemens Inc.), and laser drilled metal (Telectronics Ltd.) electrodes in that same time period.

A considerable breakthrough in the development of low threshold electrode technology occurred with the invention of the steroid eluting porous pacing electrode of Stokes, U.S. Pat. No. 4,506,680 and related Medtronic U.S. Pat. Nos. 4,577,642; 4,606,118 and 4,711,251, all incorporated herein by reference. The electrode disclosed in the Stokes '680 patent was constructed of porous, sintered platinum or titanium, although carbon and ceramic compositions were also mentioned. Proximate the electrode a plug of silicone rubber impregnated with the sodium salt of dexamethasone phosphate, or a water soluble form of other glucocorticosteroids, was placed. The silicone rubber plug allowed the release of the steroid through the interstitial gaps in the porous sintered metal electrode to reach the electrode-tissue interface and prevent or reduce inflammation, irritability and subsequent excessive fibrosis of the tissue adjacent to the electrode itself. The porous steroid eluting electrode presented a sensing (source) impedance substantially lower compared to similarly sized solid electrodes and presented significantly lower peak and chronic pacing thresholds than similarly sized solid or porous electrodes. These two advantages of the steroid eluting electrode allowed a relatively small surface area electrode of about 5.5 mm² (CAPSURE® SP Model 5023, 5523 leads sold by Medtronic, Inc.) to raise lead impedance without sacrificing the ability to sense heart activity. The smaller electrode size was important because it resulted in higher current density during stimulation pulses. This, in turn, was important because it provided more efficient stimulation of the heart tissue with lower current drain from the implanted pacemaker power source. This resulted in overall increased longevity of the implanted pacemaker system.

Lead impedance is a function of the resistance of the lead conductor and the stimulating electrode as well as the effective impedance of the electrode-tissue interface. An inefficient way or means to raise impedance is to increase the resistance of the lead conductor. This wastes current as heat. It is preferable to decrease lead current drain with more efficient control of the stimulating electrode-tissue interface impedance. This can be done by reducing the geometric surface area of the electrode. It has been widely believed that small electrodes, however, are inefficient at sensing natural depolarizations of the cardiac tissue. This is not necessarily true. The amplitude of the intrinsic cardiac depolarization signals typically the ventricular QRS and/or atrial P-wave complexes) is essentially independent of electrode size. The problem of sensing natural depolarizations therefore is that the sense amplifiers of some pulse generators have comparatively lower input impedance, some as low as 20 k$\Omega$, with typical values of about 80–100 k$\Omega$. The impedance of the QRS or P-wave signal (or "source impedance") increases as the electrode surface area decreases. Thus, a 5 mm² polished electrode will produce QRS or P-waves with about 2.5–5 k$\Omega$ source impedance (depending on the material). According to Kirchoff's law, the attenuation of the signal in the generator's amplifier is $1/(1+Z_{in}/Z_s)$ where $Z_{in}$ is the input impedance of the amplifier and $Z_s$, is the source impedance of the signal to be sensed. Thus, for a signal with a 5 k$\Omega$ source impedance into an amplifier with a 20 k$\Omega$ input impedance will have its amplitude reduced by $[1/(1+20/5)] \times 100 = 20\%$. In marginal cases, this may make the difference between being able or not being able to sense properly. Therefore, it is important to keep the source impedance low, preferable to attenuate less than 10% of the cardiac input signal, that is, $Z_s < 2222\Omega$, for a 20 k$\Omega$ amplifier.

Thus, there is a trade-off with geometric surface area of the electrode between the demands for low current drain and adequate sensing. In addition, it is desirable to achieve relatively low polarization effects to avoid distortion of the electrogram of evoked or intrinsic cardiac depolarizations or leave a postpulse potential of sufficient magnitude to be mistakenly sensed as a QRS or P-wave by the amplifier.

Recent advances in lead design have continued decreasing the exposed geometric surface area of the electrode. One such example is disclosed in U.S. patent application Ser. No. 07/887,560 filed May 18, 1992, now U.S. Pat. No. 5,282,844 and entitled "High Impedance, Low Polarization, Low Threshold Miniature Steroid Eluting Pacing Lead Electrodes" incorporated herein by reference. That application discloses a lead featuring a porous platinized steroid eluting electrode exhibiting an effective surface area in the range of 0.1 to 4.0 mm², and preferably between 0.6 to 3.0 mm². Such small electrodes, while having many desirable qualities, are relatively more difficult to consistently manufacture, especially with respect to electrode diameter and concentric dimension.

Porous platinized steroid eluting electrodes have been manufactured using a slurry process. Specifically a slurry of platinum particles suspended in a liquid organic binding agent is created. To form the electrode, a substrate, typically a straight shank of wire, is dipped at one end into the slurry. A portion of the platinum mixture sticks to the wire substrate when it is removed. The substrate is then sintered to drive off the binder and fuse the platinum particles together. Under conditions of mass production the resultant electrode is many times, however, dimensionally inconsistent, e.g. eccentric, too large or too small and thus unacceptable.

SUMMARY OF THE INVENTION

It is thus an object of the present invention to provide a substrate for an electrode which will provide increased dimensional consistency during the manufacture of the electrode.

It is a further object of the present invention to narrow the variance of the diameter and concentric dimensions of the manufactured electrode.

It is a further object of the present invention to provide a substrate for an electrode which will provide increased impedance.

It is a further object of the present invention to provide such a substrate for use with an electrode having a reduced effective surface area of a pacing electrode, i.e., in the range of 0.1 to 4.0 mm², preferably 0.6 to 3.0 mm² as to increase pacing impedance without increasing thresholds and without negatively impacting sensing capabilities.

The present invention provides a substrate for a porous platinized steroid eluting electrode which narrows the dimensional variance of the manufactured electrode without sacrificing any desired performance qualities as well as providing increased mechanical strength Specifically the present invention provides a conductive substrate having a mounting portion with a raised surface at the distal end. In the preferred embodiment, the mounting portion of the substrate is nailhead-shaped.

The present invention may be used in a body-implantable lead for the delivery of an electric stimulus to a desired body site, particularly the atrial or ventricular chambers of a patient's heart. In a preferred embodiment the lead presents a very high (greater or equal to 800 ohm) pacing impedance with low peak and chronic thresholds, low source impedance and excellent sensing with an exposed geometric surface area in the range of 0.1–4.0 mm$^2$, preferably between 0.6 and 3.0 mm$^2$, with about 1.0 mm$^2$ providing optimum performance. The lead has a pacing impedance of at least 1400±260 ohms, a source impedance of at least 1650±410 ohms in both chambers of the heart.

Both endocardial and epicardial leads may be fabricated in accordance with the teachings of the present invention.

BRIEF DESCRIPTION OF THE DRAWINGS

These and other objects and advantages of the present invention may be fully understood and appreciated in conjunction with the attached drawings and the following detailed description of the preferred embodiments where the same numerals are employed to denote the same or similar features throughout.

DETAILED DESCRIPTION OF THE DRAWINGS

As a general comment, the present invention preferably includes the use of asteroid or other drug with the electrode. The electrode may be configured to allow the drug to be eluted through and/or around the electrode in order to reach the endocardial or myocardial cells near the distal end of the pacing lead in order to reduce, if not eliminate entirely, the acute and chronic inflammation occasioned by the cellular foreign body and physical irritation response to the tip of the lead. As described in Stokes, U.S. Pat. No. 4,506,680 and related Medtronic U.S. Pat. Nos. 4,577,642; 4,606,118 and 4,711,251, mentioned above, the electrode is preferably fabricated from a body compatible electrically conductive material with or without specific steroid eluting passages but generally with a porous structure either throughout the body of the electrode or at its surface. The porosity of the electrode surface or body provides a large surface area for sensing whereas the overall dimension or shape of the exposed electrode defines a comparatively smaller surface area for stimulation. The porous structure thus presents a microscopic (or "fractal") large surface area for sensing and a macroscopic or geometrically measured very small surface area for stimulation. Acceptable electrode materials and the associated fabrication techniques employed to achieve the micro-porous structure, as well as the porosity of that structure are all set forth in the aforementioned prior art patents and in the Richter et al., U.S. Pat. No. 4,773,433; Heil Jr. et al., U.S. Pat. No. 4,819,661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603,704; Skalsky et al., U.S. Pat. No. 4,784,161; Szilagyi, U.S. Pat. No. 4,784,160, herein incorporated by reference and other patents and literature in the prior art.

The present invention concerns a stem or substrate to which an electrode of a pacing lead is mounted. The substrate of the present invention permits the electrode to be more consistently manufactured with respect to its dimensions. The substrate of the present invention also provides an advantageous mounting for the electrode mixture so that the electrode produced has a relatively higher mechanical strength than electrodes having a straight shank substrate. In addition, in the preferred embodiment, the nailhead-shaped substrate configuration of the present invention provides for a higher impedance lead to be constructed.

Figure 1:
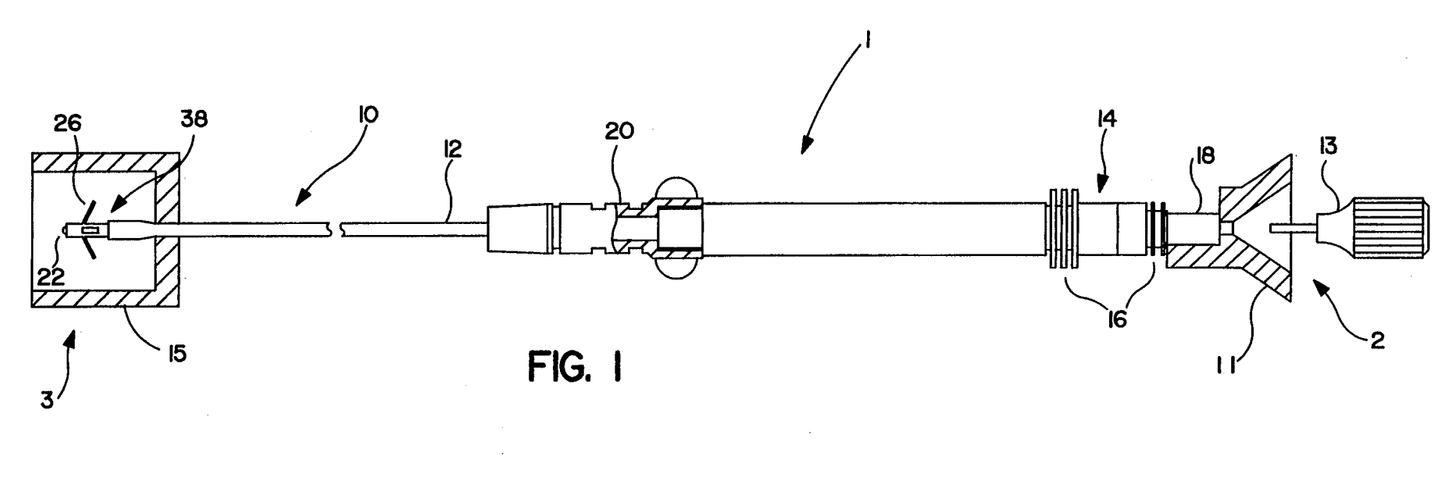
FIG. 1 shows a side plan view of an endocardial, unipolar pacing lead according to the present invention.

FIG. 1 illustrates a plan view of an exposed lead constructed in accordance with the present invention. The lead 1 includes an elongated lead body 10 covered by an insulative sleeve 12. Insulative sleeve 12 may be fabricated of any flexible biocompatible and biostable insulator especially silicone rubber or polyurethane. At the proximal end 2 of lead 1, terminal assembly 14 is adapted to couple lead 1 to an implantable pacemaker pulse generator (not shown.) Terminal assembly 14 is provided with sealing rings 16 and a terminal pin 18, all of a type known in the art. An anchoring sleeve 20 (shown partially in cross-section) slides over lead body 10 and serves as a point for suturing lead body 10 to body tissue at the insertion point of lead 1 in a fashion known in the art. Anchoring sleeve 20 and terminal assembly 14 are preferably fabricated of silicone rubber, although they may also be constructed of any other suitable biocompatible material known in the art.

Lead 1 shown in FIG. 1 further includes a stylet guide 11 and stylet assembly 13 coupled to terminal pin 18 for imparting stiffness to lead 1 during the insertion and placement of lead 1 transvenously into either the right ventricle or the right atrium of the heart (not shown.) Stylet guide 11 and stylet assembly 13 are discarded after use and before connection of terminal pin 18 to a pacemaker pulse generator (not shown.)

At distal end 3 of lead 1, a tine protector 15 is shown (in cross-section) protecting tines 26 until lead 1 is used. Tines 26 are employed to passively retain electrode 22 in position against the endocardium (not shown) as is well known in the pacing art.

Figure 7:
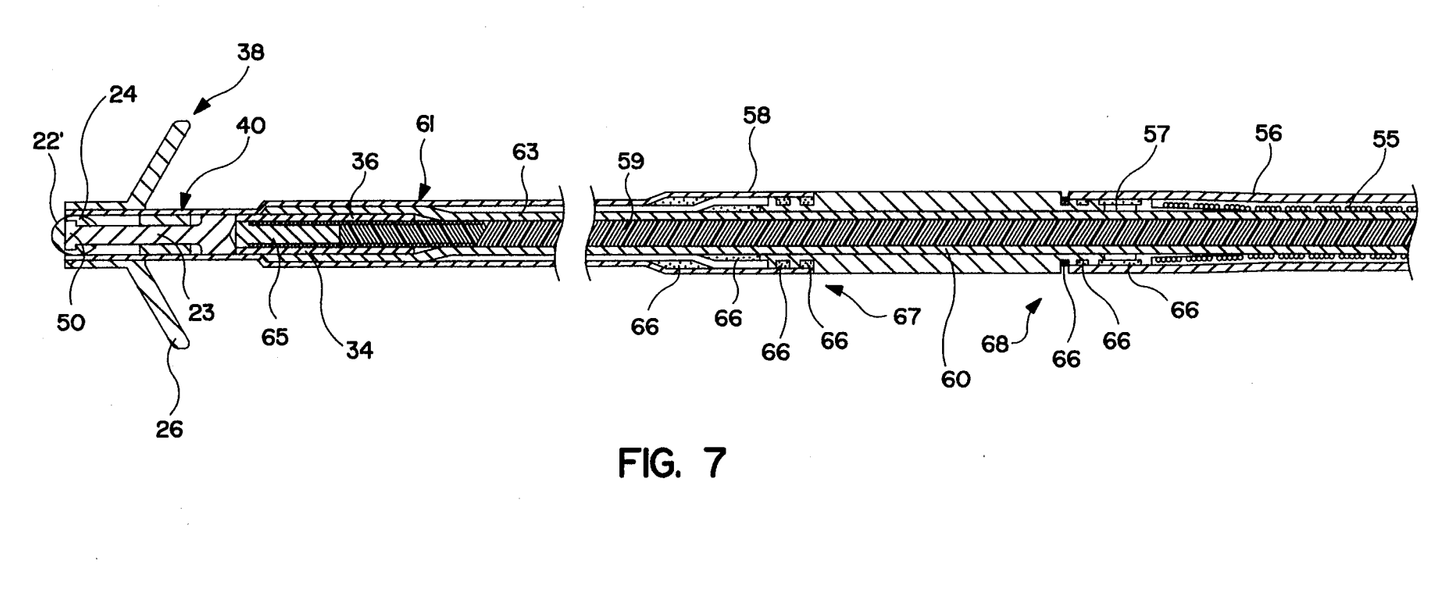
FIG. 7 shows a cross-sectional view of the distal end of an endocardial, bipolar, pacing lead according to the present invention.

Although FIG. 1 depicts a unipolar lead, the present invention may also be implemented in a bipolar lead design, as shown in FIG. 7, employing a second conductor extending from a second exposed cylindrical terminal surface area near the proximal end of the lead to an exposed ring electrode 60 spaced $\geq 8$ mm from electrode 22 as is well known in the art. The $\geq 8$ mm spacing is necessary because the current sense amplifier bandpass center frequency is about 25–30 Hz. Closer spacings are possible if the sense amplifier bandpass center frequency is shifted to higher values accordingly, and if higher gains are used.

Figure 2:
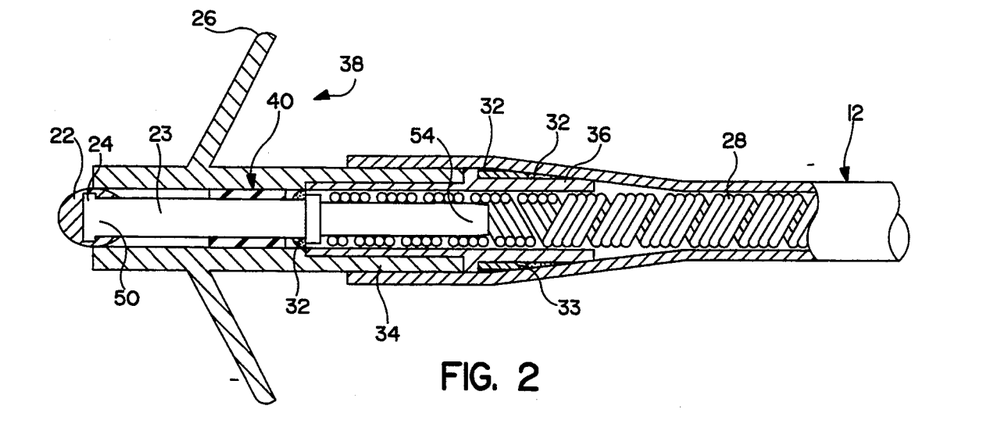
FIG. 2 shows a cross-sectional view of the distal end of the lead shown in FIG. 1.

Lead 1 of FIG. 1 includes a conductor coil 28 extending throughout, i.e., from terminal pin 18 to electrode 22. Preferably conductor coil 28 is multifilar in construction. FIG. 2 shows in cross-section the distal end of lead 1 of the present invention and the connection of conductor coil 28 to stem or substrate 23 and electrode 22. Electrode 22 is depicted as a porous platinum generally ball-shaped object covered with platinum black at the end of substrate 23. Although platinum is the preferred material for electrode 22 and substrate 23, they may additionally include or be made entirely from various other materials, including but not limited to such materials as palladium, titanium, tantalum, rhodium, iridium, carbon, vitreous carbon and alloys, oxides and nitrides of such metals or other conductive materials. Of course, some materials are incompatible with others, such as a platinum substrate with a titanium electrode, and may not be effectively used together. The limitations of specific materials for use with others is well known in the art.

As discussed above, electrode 22 is manufactured from a viscous slurry mixture of platinum splat powder and an organic binder, such as KLUCEL ™ manufactured by Aqualon Corp. of Wilmington, Del. One end of the substrate, typically a straight cylindrical wire, is dipped into the slurry mixture. The material which remains adhering to the end when the substrate is withdrawn, generally ball-like in shape, is then sintered, as is well known in the art, to draw off the organic binder and harden the platinum to substrate 23.

The present invention provides a substrate 23 having a raised surface 24 at distal end 50 to which electrode 22 is formed. It is believed raised surface 24 acts as a ledge or ridge which, along with the surface tension of the fluid electrode material before sintering, aides in consistently forming and supporting the electrode material until sintering is complete. Electrodes having less dimensional variance, as compared to electrodes having a straight shank substrate, result.

Figure 3:
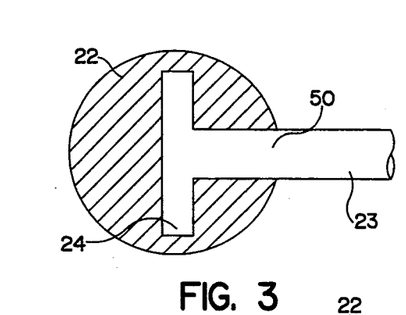
FIG. 3 shows a cross-sectional view of the distal end of the substrate used in the lead according to the present invention.
Figure 4:
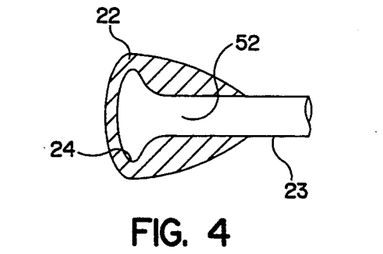
FIG. 4 shows a cross-sectional view of the distal end of another alternate embodiment of the substrate used in the lead according to the present invention.
Figure 5:
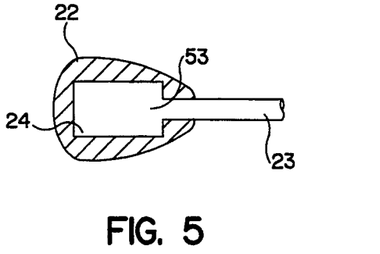
FIG. 5 shows a cross-sectional view of the distal end of another alternate embodiment of the substrate used in the lead according to the present invention.
Figure 13:
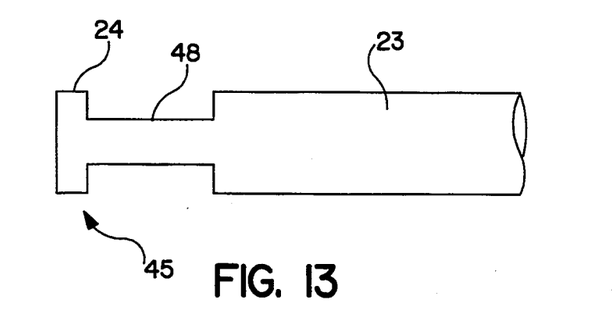
FIG. 13 shows another alternate embodiment of the substrate used in the lead according to the present invention.
Figure 14:
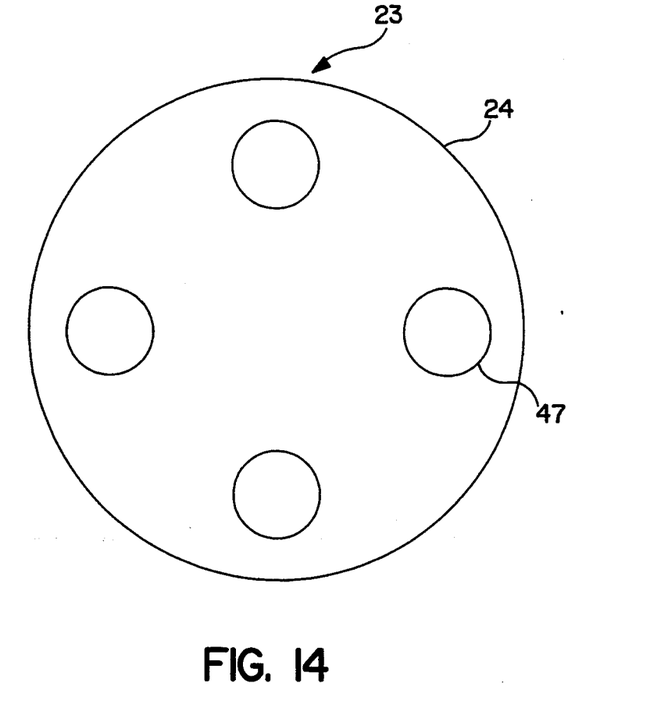
FIG. 14 shows a distal end view of an alternate embodiment of the substrate used in the lead according to the present invention.
Figure 15:
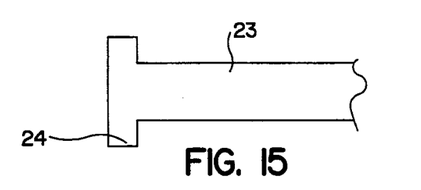
FIG. 15 shows a cross-sectional view of the distal end of another alternate embodiment of the substrate used in the lead according to the present invention.
Figure 16:
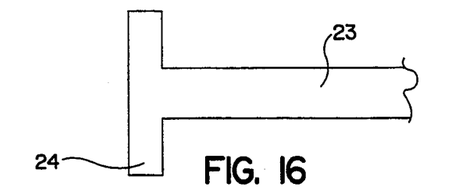
FIG. 16 shows a cross-sectional view of the distal end of another alternate embodiment of the substrate used in the lead according to the present invention.

In the preferred embodiment, substrate 23 has an annular lip or nailhead-shaped distal end 50, as depicted in FIGS. 2, 3 and 16. Nailhead shapes having additional relative proportions may further be seen in FIGS. 15, 17 and 18. Other shapes for the raised surface 24 at distal end 50 of substrate 23, such as a ridge, swab-shaped or having an annular lip, may also be used. Any shape functioning decrease dimensional variance of the manufactured electrode by a geometric configuration at the distal end 50 of the substrate 23 is within the scope of the present These shapes include, but are not limited to, the example configurations seen in FIGS. 4, 5 and 15–18. FIG. 4 depicts a substrate 23 having a matchhead-shaped distal end 52. The shape depicted in FIG. 4 has the further advantage that may be rapidly and consistently manufactured by melting an end portion of a straight shank of wire. FIG. 5 depicts a substrate having a block-shaped distal end 53. Further, as seen in FIG. 13, raised surface 24 may further be provided through provision of a recess 48 proximate distal end 45 and from which raised surface 24 relatively extends. Finally, a series of holes 47 may be provided radially about raised surface 24, as best seen in FIG. 14, to also provide for an increased elution rate of steroid from steroid silicone compound ring 40 to the distal tip of electrode 22.

Substrate 23 extends from electrode 22 end of conductor coil 28 where it is attached to end 54 of substrate 23 by crimping at point 34 of crimping member 36 at the time of manufacture. An adhesive, such as a silicone medical adhesive, may be used at various points 32 to seal against leakage of fluid, such as blood, into conductor coil 28. Insulative sleeve 12 is placed over skirt 33 and crimping member 36 as well as proximate tine assembly 38. Steroid-silicone compound ring 40 is located proximate to electrode 22.

Electrode 22 is preferably a porous platinum composition electroplated with platinum black. The porosity, together with the platinum black coating is intended to reduce source impedance and polarization.

Steroid-silicone compound ring 40 forms a monolithic controlled release device when it is loaded with an anti-inflammatory agent, e.g., asteroid dexamethasone sodium phosphate. The steroid also is deposited within the pores of electrode 22 by application of a solution of 200 mg U.S.P. dexamethasone sodium phosphate dissolved in 5.0 cc isopropanol and 5.0 cc distilled or deionized water as described in the aforementioned Stokes' patents. Weight and composition of steroid-silicone compound ring 40 as well as the electrode surface area are critical to the overall performance of electrode 22. In a preferred embodiment electrode 22 has a macroscopic surface area of less than 4.0 mm² exposed to the body tissue or fluids or both and more preferably, but not limited to, in the range of 0.10 and 4.0 mm². The surface of electrode 22 exposed to the body tissue or fluids or both is generally hemispherical. The small geometric macroscopic electrode size is intended to produce very high pacing impedance. The porous surface configuration together with platinum black electroplating and steroid contribute to a microscopically large surface area for low polarization, low source impedance and low thresholds. The porous surface also facilitates the retention of steroid and adhesion of the platinum black to the electrode surface. The electrode 22, therefore, permits steroid to elute therethrough. The electrode 22 and lead, especially tine assembly 38, may preferably be dimensioned, moreover, to further allow steroid to elute around the electrode 22, i.e., between electrode 22 and tine assembly 38.

Figures 19, 20:
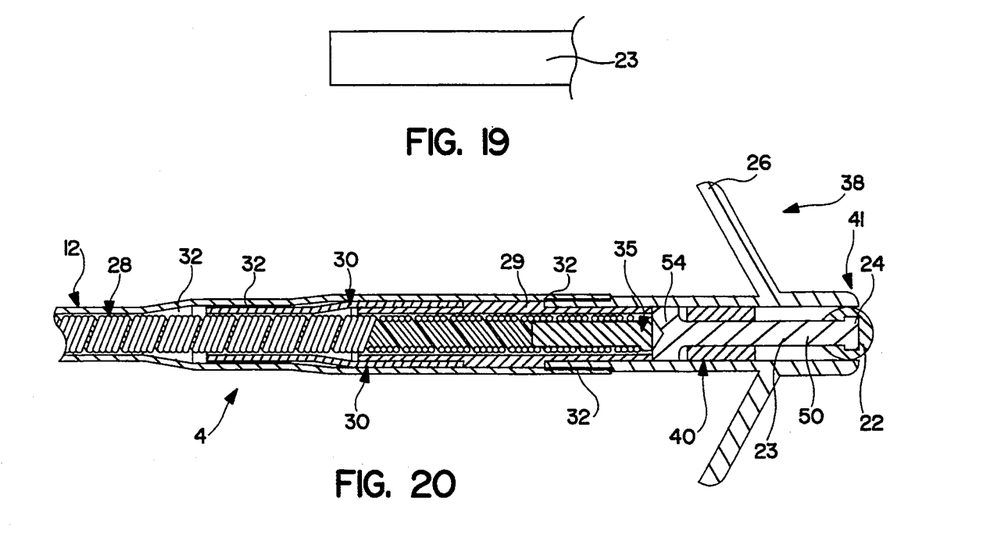
FIG. 19 shows a cross-sectional view of the distal end of a straight stem substrate used in the prior art.
FIG. 20 shows a cross-sectional view of the distal end of an alternate embodiment of a lead according to the present invention.

FIG. 20 depicts an alternate embodiment of a lead constructed using the substrate of the present invention. As seen lead 1 is constructed from multifilar conductor coil 28 covered by insulative sleeve 12. Distal end of conductor coil 28 is connected to electrode 22 by crimp plug 35. Specifically, conductor coil 28 is connected onto crimp plug 35 by crimping skirt 29. Skirt 29 is preferably made of platinum. Attached to distal end of skirt 29 is stiffener 30. Crimp plug 35 is connected to distal end 54 of substrate 23 and thus to electrode 22. Lead 4 is sealed against leakage of fluids by application at various points 32 of adhesive, such as a silicone medical adhesive. Electrode 22 and substrate 23 are substantially similar to electrode 22 as shown in FIG. 2 and preferably incorporate use of a steroid-silicone compound ring 40. As seen tine assembly 38 features rounded or radiused shoulders 41. This construction presents a wider profile of the tip of electrode 22 to tissue (not shown) as compared to the lead construction seen in FIG. 2. This configuration thereby facilitates contact of tissue (not shown) to electrode 22.

Figure 6:
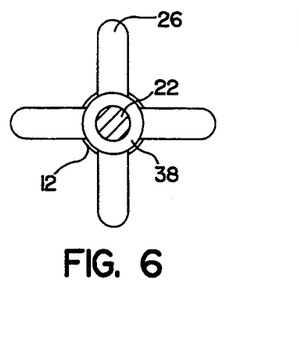
FIG. 6 shows an end plan view of the distal end of the lead shown in FIG. 1.
Figure 8:
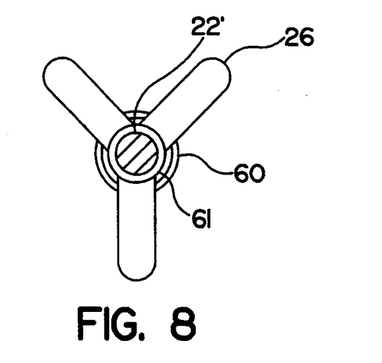
FIG. 8 shows an end plan view of the distal end of the lead shown in FIG. 7.

FIGS. 7 and 8, depict a still further alternate design of the of the present invention. Lead 1 is constructed in similar fashion to lead 1 of FIGS. 1,2 and 6 and, to the extent possible, the same numerals will be employed to describe the same or equivalent elements of these two embodiments of the lead. The principle difference between the lead depicted in FIGS. 1,2 and 6 and the lead depicted in FIGS. 7 and 8 is that the lead of FIGS. 7 and 8 is bipolar, possessing a ring electrode 60 spaced from electrode 22'. As seen, the lead of FIG. 7 is constructed using one pair of multifilar, commonly wound, separately insulated conductor coils 55, 59. Outer coil 55 is covered by outer insulative tubing 56 and insulated from inner coil 59 by inner insulative tubing 63. Insulative tubing 56, 63 is preferably made from silicone or a urethane material. Outer coil 55 is connected to ring electrode 60. Insulative tubing 56 is sealed by application a various points 66 of an adhesive, such as a silicone medical adhesive. Spacer tubing 61 covers inner coil 59 and inner insulative tubing 63 between ring electrode 60 and distal end of lead. Inner coil 59 connects to electrode 22' through crimp core 65 and crimp member 36, which is crimped at point 34 to inner coil 59. Crimp core 65, in turn, connects to substrate 23 and hence electrode 22'. Electrode 22' is fabricated of the same materials and treated in the same fashion as electrode 22 of the embodiment of FIGS. 1,2 and 6. FIG. 8 shows an end plan view of the distal end of the bipolar lead shown in FIG. 7. FIGS. 7 and 8 thus illustrate a bipolar embodiment of the pacing lead constructed and manufactured according to the present invention.

Figure 9:
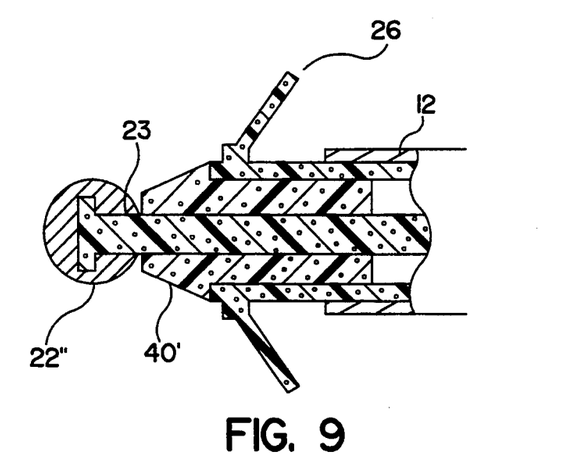
FIG. 9 shows a cross sectional view of the distal end portion of a further embodiment of a lead according to the present invention.

FIG. 9 depicts a sectional view of a further embodiment of the present invention. As seen lead 1 features electrode 22" attached to substrate 23 extending back to a similar connection with a coiled wire conductor (not illustrated). Electrode 22" is virtually fully exposed as is a portion of the distal end of steroid-silicone compound ring 40'. As is apparent, electrode 22" depicted in FIG. 9 may be employed in either endocardial or epi/myocardial lead designs where electrode 22 may penetrate myocardial tissue. The exposed surface of steroid-silicone compound ring 40' thus allows for steroid elution in a path both through and around electrode 22".

Figure 10:
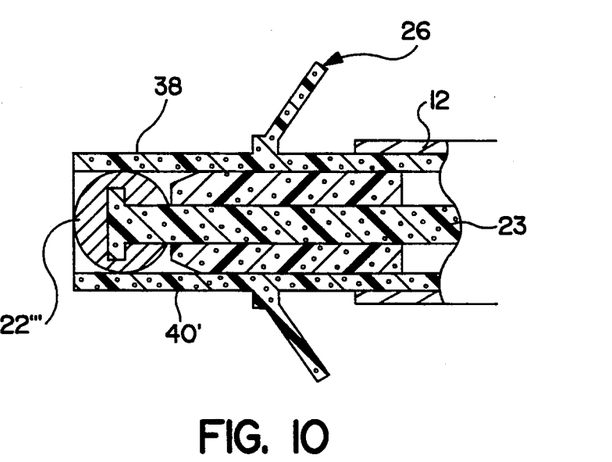
FIG. 10 shows a cross-sectional view of the distal end portion of a further embodiment of a lead according to the present invention.

FIG. 10 depicts a still further embodiment of the present invention. Electrode 22'" of FIG. 10 is a modification of electrode 22 depicted in FIGS. 1,2 and 6 except that, unlike electrode 22" depicted in FIG. 9, electrode 22'" is fully retracted within the distal portion of tine assembly 38. The inside diameter of the distal end of the lead 1, that is the inside diameter of tine assembly 38, is preferably 0.040 inches which equals a 0.8 mm² orifice. Only a hemispheric portion of the surface of electrode 22'" is exposed in this embodiment of the invention.

The aforementioned embodiments of the present invention are all illustrated as endocardial pacing leads wherein the electrode or lead tip may or may not be designed to pass through the endocardium and into the myocardium of the heart. In substitution for the tined fixation mechanisms shown, any of the endocardial lead embodiments may be provided with active screw-in fixation mechanisms.

Figure 11:
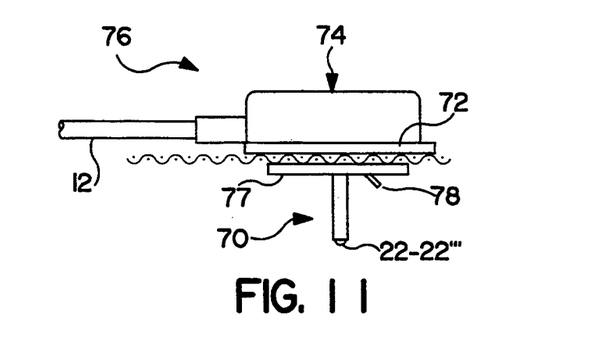
FIG. 11 shows a plan view of the distal portion of a bipolar epicardial pacing lead according to the present invention.
Figure 12:
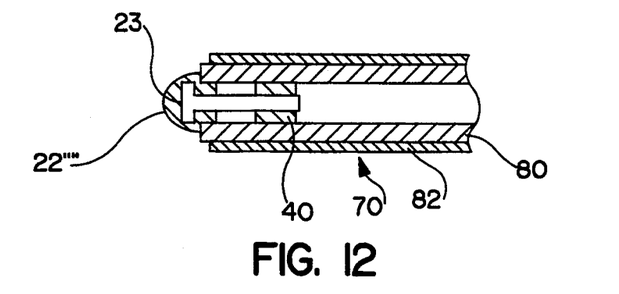
FIG. 12 shows a cross-sectional view of the distal end of an electrode, preferably employed in the lead of FIG. 11.

FIGS. 11 and 12 depict a further embodiment wherein the concept of the present invention is embodied in a bipolar epicardial pacing lead 76 wherein electrode 22"" is mounted on a spike 70 extending from a platform 72 of an epicardial lead body 74 to penetrate into the myocardium (not shown.) Electrode 77 sits atop myocardium (not shown) and may be sutured thereto. While not specifically shown, the lead of FIG. 11 may be affixed in place by fixation hooks or screws (partially shown at 78) or sutures. The specific configuration of electrode 22"" may further take the form of any of electrodes 22–22'" previously described with the exception that the outer surface or tubular member of spike 70 may need to be stiff enough to allow electrode 22"" to penetrate the epicardial membrane.

Preferably electrode 22"" and spike 70 are constructed as shown in FIG. 12. Spike 70 preferably comprises a hollow metal tube 80 having steroid-silicone compound ring 40 located at any point therein between electrode 22"" and the point where tube 80 is mechanically and electrically connected to conductor coil 28 (not shown) within epicardial lead body 74. Electrode 22"" is attached to tube 80, and the exterior of tube 80 is insulated by outer tube 82. Steroid-silicone compound ring 40 eludes steroid through electrode 22"".

Bipolar epicardial pacing lead 76 shown in FIG. 11 may further feature an electrode soaked with steroid, in the same fashion as electrode 22 as seen in FIG. 1. The epicardial lead 76 may also be constructed in unipolar fashion substituting a porous fabric for electrode 77 to allow fixation to the epicardium by fibrotic tissue ingrowth. Said unipolar leads may also be fixed to the heart by sutures, obviating the need for the fabric mesh. Such leads may otherwise possess the features of Medtronic, U.S. Pat. No. 4,010,758 and designs discussed in a paper by K. Stokes, "Preliminary Studies on a New Steroid Eluting Epicardial Electrode", *PACE*, Vol. 11, pp. 1797–1803, November 1988, incorporated herein by reference.

As discussed above, electrode 22 is typically manufactured using a slurry process. In the preferred method a viscous slurry mixture is prepared of platinum splat powder and an organic binder, such as KLUCEL TM manufactured by Aqualon Corp. of Wilmington, Del. having the relative composition 62.5 weight percent platinum and 37.5 weight percent KLUCEL TM. Substrate 23, according to any of the embodiments discussed above, is dipped into the slurry mixture. Specifically distal end 50 having raised surface 24 is dipped so that slurry mixture envelopes raised surface 24. Substrate 23 is next removed from the slurry mixture. The slurry material which remains adhering to raised surface 24 when substrate 23 is withdrawn, generally ball-like in shape, is then sintered, as is known in the art, to draw off the organic binder and harden the platinum to substrate 23. In the preferred method substrate 23 is sintered at 1357 degrees celsius for one hour.

It is believed raised surface 24 acts as a ledge which, along with the surface tension of the slurry mixture before sintering, aides in consistently forming and supporting the electrode material until sintering is complete. Through raised surface 24, therefore, a more dimensionally consistent, both concentrically and with respect to width, electrode 22 is produced.

Electrode 22 may further be fabricated using a fluidized bed process, Specifically a bed of platinum splat powder is fluidized, preferably by a gas such as nitrogen. Substrate 23 is prepared by dipping the end of substrate 23 having raised surface 24 into a binder, such as KLUCEL TM manufactured by Aqualon Corp. of Wilmington, Del., so that the raised surface 24 is completely enveloped, and then dipping it into a fluidized bed of platinum splat powder. The material adhering to raised surface 24 when substrate 23 is withdrawn, generally ball-like in shape, is then sintered, as is known in the art, to draw off the organic binder and harden the platinum splat powder to substrate 23. In the preferred method substrate 23 is sintered at 1357 degrees celsius for one hour.

The previously described embodiments are illustrative of a lead electrode of the present invention. In the preferred embodiment the present invention is used in and to manufacture very small diameter tip electrodes and pacing leads. As previously indicated, the prior art had progressed to the point where the lower limit for effective macroscopic surface areas was believed to be within the range between 5.5 mm$^2$ and 8 mm$^2$. Studies conducted with steroid free, small macroscopic surface area porous electrodes have confirmed the expectation and findings of the aforementioned prior investigators in the field.

Test results of electrodes manufactured using both the slurry method and the fluidized bed method show the significant advantage with respect to electrode dimensional consistency offered by the present invention. Shown below is a summary of the data from diametric measurements for electrodes made using substrates having a raised surface, depicted in FIGS. 15–18 and a straight-stem substrate, depicted in FIG. 19. All the substrates depicted in FIGS. 15–19 are circular in axial cross section and are depicted in relative sizes.

Figure 17:
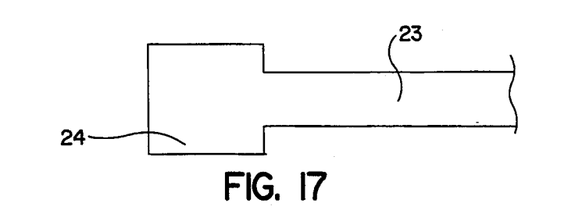
FIG. 17 shows a cross-sectional view of the distal end of another alternate embodiment of the substrate used in the lead according to the present invention.
Figure 18:
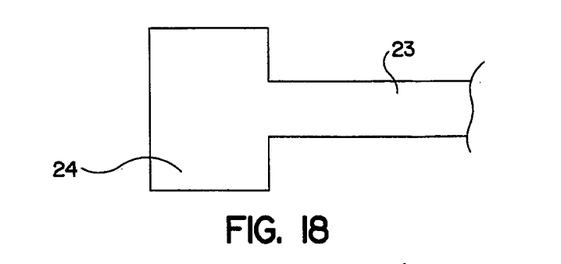
FIG. 18 shows a cross-sectional view of the distal end of another alternate embodiment of the substrate used in the lead according to the present invention.

| Electrode using substrate shown in FIG. | Number tested | Mean (inches) | Standard Deviation (inches) |
| --- | --- | --- | --- |
| FIG. 15 slurry method | 10 | 0.0283 | 0.0024 |
| FIG. 16 slurry method | 10 | 0.0344 | 0.0024 |
| FIG. 17 slurry method | 10 | 0.0299 | 0.0013 |
| FIG. 18 slurry method | 9 | 0.0408 | 0.0009 |
| FIG. 16 fluidized bed method | 10 | 0.0409 | 0.0017 |
| FIG. 18 fluidized bed method | 10 | 0.0391 | 0.0021 |
| FIG. 19 (straight stem) slurry method | 234 | 0.0378 | 0.0064 |

In addition, test results show that a lead constructed using the substrate configuration shown in FIG. 16 had greater impedance (1657 ohms with a standard deviation of 91 ohms) than a comparably dimensioned lead constructed using a straight stem substrate shown in FIG. 18 (1255 ohms with a standard deviation of 67 ohms.)

Thus it can be seen that very small electrodes may be more consistently constructed and manufactured according to the present invention which satisfy the aforementioned desirable characteristics of a pacing lead, i.e. low stimulation thresholds, relatively low polarization, good to excellent sensing, and adequately low source impedance. Moreover, leads manufactured using the preferred embodiment of the present invention, as seen in FIG. 2 and best seen in FIG. 16 further offer improved pacing impedance over prior leads using straight stem substrate. Higher pacing impedance prolongs the longevity of pacing pulse generators and allows for the miniaturization of their components.

While the embodiments of the present invention have been described in particular application to cardiac pacing, it will be understood the invention may be practiced in other electrode-technologies where the aforementioned characteristics are desirable, including neurological and muscle stimulation applications.

The invention has been described in detail with particular reference to the preferred embodiments thereof, but it will be understood variations and modifications can be effected within the scope of the following claims.

What is claimed is:

1. A method of manufacturing an electrode for a lead used to stimulate and sense a body comprising the steps of:

forming a raised surface on a distal end of a conductive stem;

preparing a slurry mixture containing at least one conductive material;

introducing at least a portion of said raised surface of said conductive stem into said slurry mixture;

withdrawing said portion of said raised surface of said conductive stem from said slurry mixture such that a portion of said slurry mixture envelopes said raised portion of said conductive stem and covers said distal end of said substrate in a non-uniform thickness; and sintering said portion of said slurry mixture enveloping said raised surface.

2. The method of claim 1 wherein said forming said raised surface on a distal end of a conductive stem comprises deforming with heat said distal end of said conductive stem.

3. The method of claim 2 wherein said deforming with heat comprises melting said distal end of said conductive stem.

4. The method of claim 1 wherein said forming said raised surface on said distal end of said conductive stem comprises mechanically deforming said distal end of said conductive stem.

5. The method of claim 1 wherein said conductive material is from the class of materials consisting essentially of platinum, palladium, titanium, tantalum, rhodium, iridium, carbon, vitreous carbon and alloys, oxides or nitrides of such metals.

6. The method of claim 1 wherein said raised surface comprises a nailhead-shaped configuration.

7. The method of claim 1 wherein said mixture comprises a slurry containing at least one binder.

8. A method of manufacturing an electrode for a lead used to stimulate and sense a body comprising the steps of:
providing a cylindrical conductive stem having a first diameter;
forming a raised surface on a distal end of the conductive stem, the raised surface having a second diameter, the second diameter being greater than the first diameter;
preparing a mixture containing at least one conductive material;
introducing at least a portion of the raised surface of the conductive stem into the mixture;
withdrawing the portion of the raised surface of the conductive stem from the mixture such that a portion of the mixture envelopes the raised portion of the conductive stem, the portion of the mixture enveloping the raised portion of the conductive stem having a third diameter, the third diameter being greater than the second diameter; and
sintering the portion of the mixture enveloping the raised surface.

9. The method of claim 8 the portion of the mixture enveloping the raised portion of the conductive stem envelopes the raised portion in a non-uniform thickness.

10. A method of manufacturing an electrode for a lead used to stimulate and sense a body comprising the steps of:
providing a conductive stem having a first diameter;
forming a raised surface at a distal end of the conductive stem, the raised surface having a second diameter, the second diameter being equal to or greater than the first diameter;
preparing a mixture containing at least one conductive material;
introducing at least a portion of the raised surface of the conductive stem into the mixture;
withdrawing the portion of the raised surface of the conductive stem from the mixture such that a portion of the mixture envelopes the raised portion of the conductive stem, the portion of the mixture enveloping the raised portion of the conductive stem having a third diameter, the third diameter being greater than the second diameter, the mixture enveloping the raised portion of the conductive stem in a non-uniform thickness; and
sintering the portion of the mixture enveloping the raised surface.

11. The method of either claims 8 or 10 wherein the forming the raised surface on the distal end of the conductive stem comprises mechanically deforming the distal end of the conductive stem.

12. The method of either claims 8 or 10 wherein the conductive material is from the class of materials consisting essentially of platinum, palladium, titanium, tantalum, rhodium, iridium, carbon, vitreous carbon and alloys, oxides or nitrides of such metals.

13. The method of either claims 8 or 10 wherein the mixture comprises a slurry containing at least one binder.

14. The method of either claims 8 or 10 wherein the mixture comprises a fluidized bed of the conductive material and a gas.

* * * * *